United States Patent
Meyer et al.

(10) Patent No.: US 7,203,543 B2
(45) Date of Patent: Apr. 10, 2007

(54) METHOD AND SYSTEM FOR DETECTING CAPTURE USING A CORONARY VEIN ELECTRODE

(75) Inventors: Scott A. Meyer, Rochester, MN (US); Haris J. Sih, Minneapolis, MN (US); Paul A. Haefner, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 453 days.

(21) Appl. No.: 10/278,732

(22) Filed: Oct. 23, 2002

(65) Prior Publication Data

US 2004/0082975 A1    Apr. 29, 2004

(51) Int. Cl.
*A61N 1/37* (2006.01)
*A61N 1/362* (2006.01)

(52) U.S. Cl. .......................... 607/28; 607/27
(58) Field of Classification Search ............... 607/27, 607/28; 600/522; 128/902
See application file for complete search history.

(56) References Cited

U.S. PATENT DOCUMENTS

| | | | | |
|---|---|---|---|---|
| 5,431,693 A | * | 7/1995 | Schroeppel | 607/28 |
| 6,101,416 A | | 8/2000 | Sloman | 607/28 |
| 6,128,535 A | | 10/2000 | Maarse | 607/28 |
| 6,363,281 B1 | | 3/2002 | Zhu et al. | 607/28 |
| 6,505,071 B1 | * | 1/2003 | Zhu et al. | 607/28 |
| 6,512,953 B2 | * | 1/2003 | Florio et al. | 607/28 |
| 6,754,535 B2 | * | 6/2004 | Noren et al. | 607/28 |
| 2001/0049542 A1 | * | 12/2001 | Florio et al. | 607/28 |
| 2003/0050671 A1 | * | 3/2003 | Bradley | 607/27 |
| 2003/0083711 A1 | * | 5/2003 | Yonce et al. | 607/27 |
| 2003/0195579 A1 | * | 10/2003 | Bradley et al. | 607/27 |

* cited by examiner

*Primary Examiner*—Robert E. Pezzuto
*Assistant Examiner*—Tammie K. Heller
(74) *Attorney, Agent, or Firm*—Hollingsworth & Funk, LLC

(57) ABSTRACT

A method and device provide for determining capture in multiple chambers of a patient's heart using an electrode inserted into a coronary vein of the patient's heart. The coronary vein electrode is positioned adjacent to multiple heart chambers and is responsive to cardiac signals originating in the multiple chambers. The coronary vein electrode may be coupled to a single sense amplifier to detect the cardiac signals. Pace pulses may be applied to multiple heart chambers simultaneously or according to a phased timing sequence. Cardiac signals responsive to the pace pulses sensed using the coronary vein electrode may be used to verify capture in the multiple chambers of the heart.

26 Claims, 14 Drawing Sheets

METHOD AND SYSTEM FOR DETECTING CAPTURE USING A CORONARY VEIN ELECTRODE

FIELD OF THE INVENTION

The present invention relates generally to implantable medical devices and, more particularly, to verifying capture in multiple chambers of the heart using one or more electrodes positioned in a coronary vein of the heart.

BACKGROUND OF THE INVENTION

Rhythmic contractions of a healthy heart are normally controlled by the sinoatrial (SA) node, specialized cells located in the superior right atrium. The SA node is the normal pacemaker of the heart, typically initiating 60–100 heart beats per minute. When the SA node is pacing the heart normally, the heart is said to be in normal sinus rhythm (NSR).

A heart rhythm that deviates from normal sinus rhythm is an arrhythmia. Arrhythmia is a general term used to describe heart rhythm disturbances arising from a variety of physical conditions and disease processes. Bradycardia occurs when the heart rhythm is too slow and has a number of etiological sources including tissue damage due to myocardial infarction, exposure to toxins, electrolyte disorders, infection, drug effects, hypoglycemia or hypothyroidism. Bradycardia also may be caused by sick sinus syndrome, wherein the SA node loses its ability to generate or transmit an action potential to the atria.

Supraventricular arrhythmias originate in the atria or surrounding tissues (vena cavae, pulmonary veins, etc.) resulting in a rapid atrial rate. One mechanism for supraventricular tachycardia is an accessory pathway between the ventricular and atrial tissue. The accessory pathway, in combination with the normal AV nodal pathway, forms a conducting loop that can support reentry. The reentrant wave circulates through the pathway and elevates the heart rate. Atrial flutter is another type of supraventricular arrhythmia and arises when an electrical wavefront circulates around an anatomical or functional obstacle in the atrial myocardium. Atrial fibrillation occurs when electrical impulses initiate in the atria at irregular intervals and usually at a rate of greater than 300 impulses per minute. As a result, impulses reaching the AV node, and thus the ventricles, are also irregular, causing irregular contractions of the ventricles at an increased rate.

Ventricular tachycardia occurs when impulses are initiated in the ventricular myocardium with a rate more rapid than the intrinsic rate of the SA node. Ventricular tachycardia (VT) is characterized by a rapid heart beat and typically results from damage to the ventricular myocardium from a myocardial infarction. Ventricular tachycardia can quickly degenerate into ventricular fibrillation (VF). Ventricular fibrillation is a condition denoted by extremely rapid, uncoordinated contractions of the ventricles. The rapid and erratic contractions of the ventricles degrades the ability of the ventricles to effectively pump blood to the body and the condition is fatal unless the heart is returned to sinus rhythm within a few minutes.

Implantable cardiac rhythm management (CRM) devices may incorporate both defibrillation and pacemaker circuitry used to treat patients with serious arrhythmias. CRM devices typically include circuitry to sense signals from the heart and a pulse generator for providing electrical stimulation to the heart. Leads extending into the patient's heart are connected to electrodes that contact the myocardium for sensing the heart's electrical signals and for delivering stimulation to the heart in accordance with various therapies for treating the arrhythmias described above.

Pacemakers deliver low energy electrical pace pulses timed to assist the heart in producing a contractile rhythm that maintains cardiac pumping efficiency. Pace pulses may be intermittent or continuous, depending on the needs of the patient. Defibrillators apply one or more high energy pulses to the heart to terminate a tachyarrhythmia by shocking the heart into a normal rhythm.

There exist a number of categories of pacemaker devices, with various modes for sensing and pacing the heart. Single chamber pacemakers pace and sense one heart chamber. Dual chamber pacemakers may pace and sense two chambers of the heart. Standard dual chamber pacemakers include electrodes positioned in the right atrium and right ventricle to provide atrial and ventricular pacing. In cardiac resynchronization devices, a multichamber pacemaker may include electrodes positioned to contact cardiac tissue within or adjacent to both the left and the right ventricles for pacing both the left and right ventricles. This type of device allows bi-ventricular pacing therapy to be applied, for example, to coordinate ventricular contractions when a patient suffers from congestive heart failure (CHF). Furthermore, a pacemaker may include electrodes positioned to contact tissue within or adjacent to both the left and the right atria to enable bi-atrial pacing. Bi-atrial pacing therapy may be used, for example, to control atrial tachyarrhythmias. Future devices may pace different combinations of the four chambers or even multiple sites within the same chamber to achieve optimal coordination of contraction, arrhythmia suppression, or control of cardiac remodeling.

When a pace pulse produces a contractile response in a heart, the contractile response is typically referred to as capture, and the electrical waveform corresponding to capture is denoted an evoked response. A pace pulse must exceed a minimum energy value, denoted the capture threshold, to produce a contraction. Pacing therapy applied to multiple sites on the heart, such as the bi-ventricular or bi-atrial pacing therapies discussed above, produces a change in the temporal contraction pattern. When a pacing pulse is closely coupled to intrinsic cardiac electrical activity, the result is fusion. The evoked response from fusion beats may be confused with either capture or noncapture depending on the coupling interval between the intrinsic and paced electrical waveforms. It is desirable for a pace pulse to have sufficient energy to produce a contractile response in the heart chambers stimulated without expending energy in excess of the capture threshold. Accurate detection of the capture threshold is required for efficient pace energy management. If the pace pulse energy is too low, the pace pulses may not reliably produce a contractile response in the heart resulting in ineffective pacing. If the pace pulse energy is too high, the result may be patient discomfort as well as shorter battery life.

Capture detection, including fusion management, allows the cardiac rhythm management system to verify whether capture occurs in the stimulated heart chamber or chambers following a pacing pulse. In particular, capture detection for multiple heart chambers may be used in conjunction with bi-ventricular, bi-atrial pacing, or multisite pacing therapies. If loss of capture is detected, the cardiac rhythm management system may deliver a back-up pulse at a higher energy level to ensure capture and subsequently initiate a threshold test to reset the pacing output to a safe level.

SUMMARY OF THE INVENTION

For the reasons stated above, and for other reasons stated below which will become apparent to those skilled in the art upon reading the present specification, there is a need in the art for a method and device that reliably and accurately detects capture in multiple chambers of a patient's heart using a minimum number of electrodes and associated circuitry. Various embodiments of the invention involve a system and method for verifying capture in a patient's heart when multi-chamber pacing therapies, such as bi-ventricular or bi-atrial pacing therapies, are applied to the heart.

According to one aspect of the invention, a coronary vein (CV) electrode is positioned in a coronary vein adjacent to multiple heart chambers. Capture of multiple chambers responsive to simultaneous or phased stimulation pulses may be detected by sensing an evoked response at the coronary vein electrode. The evoked response will be a composite of the electrical activity generated by the individual stimuli. The pattern of electrical activation, and therefore the composite evoked response, will depend on whether capture occurs at individual sites. The differences in the composite evoked response signal may be used to detect loss of capture at the individual pacing sites.

In accordance with an embodiment of the invention, a method for detecting capture in multiple chambers of a patient's heart involves sensing, at a location in the coronary venous system of the patient's heart, a cardiac signal responsive to stimulation signals applied to multiple chambers of the patient's heart. The method further involves determining if capture occurs in each of the cardiac chambers using the signal sensed at the location in the coronary venous system.

Another embodiment of the invention provides a body implantable device including a lead system, a detector coupled to the lead system, and a control circuit coupled to the detector system. The lead system includes a coronary vein electrode and one or both of ventricular electrodes and atrial electrodes. The lead system conducts stimulation signals to a patient's heart. The sensing circuit includes a coronary vein sense amplifier that receives a cardiac signal sensed by the coronary vein electrode in response to the stimulation signals. The detector circuit uses the cardiac signal to determine if capture at each pacing site occurs.

In yet another embodiment of the invention, a system for detecting capture in multiple chambers of a patient's heart includes means for sensing, at a location in the coronary venous system of the patient's heart, a cardiac signal in response to multiple stimulation signals applied to the patient's heart and means for determining if capture occurs at each stimulation site using the sensed cardiac signal.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
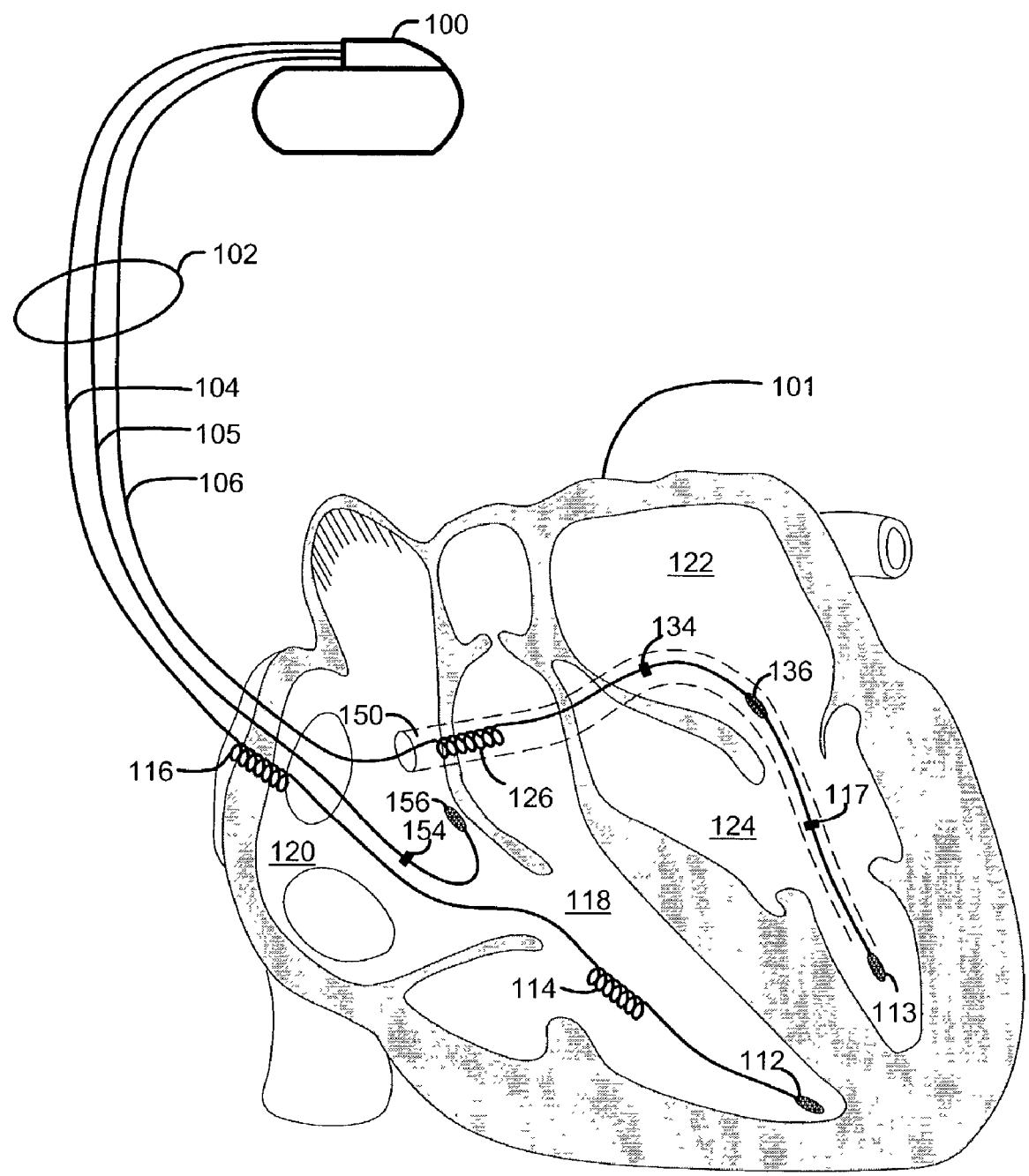
FIG. 1 is a partial view of one embodiment of an implantable medical device with an endocardial lead system extending into the heart with electrodes positioned at multiple locations of the heart which can include locations in two or more of the left atrium, left ventricle, right atrium, right ventricle, the superior vena cava and the coronary sinus.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In general, pacing pulses may be applied to any of the heart chambers in various combinations, depending on the type of therapy required. Pacing pulses may be applied simultaneously or phased in sequence to two or more pacing sites. For example, patients suffering from chronic heart failure may benefit from therapy including phased or simultaneous pacing pulses applied to both the left and right ventricles to coordinate the ventricular contractions. Furthermore, it has been shown that synchronously pacing the left and right atria may prevent atrial fibrillation.

In modern cardiac rhythm management systems, the pacing stimulation energy is typically a programmable parameter that may be adjusted to conform to a patient's needs. It is generally desirable to pace the heart using the lowest stimulation energy that reliably produces a contractile response. Pacing at an energy level that captures the heart without expending excess energy promotes patient comfort and lengthens battery life.

A patient's capture threshold may change over time, and some advanced pacemakers are capable of periodically assessing a patient's capture threshold through an autocapture procedure. Autocapture pacemakers perform an automated threshold test by ramping down the stimulation energy applied to the heart until a loss of capture is detected. The optimum pacing stimulation may then be selected as the lowest pacing energy reliably generating capture plus a reasonable margin of safety.

When the heart contracts following a pace pulse, capture occurs and a cardiac signal, denoted the evoked response, is produced. The presence of an evoked response may be used to determine if a particular pace pulse produced a heart contraction. An evoked response may be detected by monitoring the pace pulses and examining the electrical signals following the pace pulses for indications of a contractile response.

When pacing and sensing from the same electrode, the evoked response may be difficult to detect and identify because the evoked response may be very small in contrast to the immediately preceding pace pulse. In addition, the evoked response may be obscured by lead polarization effects that occur after a pace pulse. Lead polarization is caused by electrochemical reactions occurring where the electrode contacts the surrounding aqueous medium. Lead polarization produces a pacing artifact afterpotential characterized by a large electrical signal immediately following a pace pulse. The pacing artifact may be several times larger than the evoked response. Capture detection may require additional circuitry or sensors used to sense the evoked response, thereby increasing the complexity and cost of a device, particularly when capture detection is required in multiple heart chambers or at multiple pacing sites.

The embodiments of the present system illustrated herein are generally described as being implemented in a cardiac rhythm management (CRM) device incorporating a pacemaker that may operate in numerous pacing modes known in the art. The present invention provides a system and method for verifying capture following pace pulses delivered to multiple heart chambers. Capture detection is implemented using an electrode located adjacent to multiple heart chambers and sensing the cardiac signals responsive to pace pulses delivered to the multiple heart chambers. The use of a single sensing vector to detect capture in multiple chambers reduces the complexity and cost of the CRM device. The systems and methods of the present invention may be implemented in CRM devices that pace the heart and sense cardiac activity, such as implantable cardioverters/defibrillators, pacemakers, cardiac resynchronization devices, cardiac monitors, remote patient management systems, and device programmers, for example.

Capture verification in multiple chambers or at multiple pacing sites may be used to determine the optimal energy of the pace pulses delivered to the multiple chambers. Additionally, capture verification may be used to control back up pacing initiated when pace pulses delivered to the heart fail to evoke a contractile response. These and other applications may be enhanced by employment of the systems and methods of the present invention.

In one embodiment, a CRM device configured as a dual chamber defibrillator and pacemaker operates to detect capture in accordance with the principles of the present invention. Various types of multiple chamber CRM devices are known in the art and may be used to implement a capture verification methodology of the present invention. Although the present system is described in conjunction with a CRM device having a microprocessor-based architecture, it will be understood that the CRM device may be implemented in any logic-based architecture, if desired.

Referring now to FIG. 1 of the drawings, there is shown one embodiment of a medical device system which includes a CRM device 100 electrically and physically coupled to an intracardiac lead system 102. The intracardiac lead system 102 is implanted in a human body with portions of the intracardiac lead system 102 inserted into a heart 101. The intracardiac lead system 102 is used to detect and analyze electric cardiac signals produced by the heart 101 and to provide electrical energy to the heart 101 under certain predetermined conditions to treat cardiac arrhythmias.

The intracardiac lead system 102 includes one or more electrodes used for pacing, sensing, or defibrillation. In the particular embodiment shown in FIG. 1, the intracardiac lead system 102 includes a right ventricular lead system 104, a right atrial lead system 105, and a left atrial/ventricular lead system 106. In one embodiment, the right ventricular lead system 104 is configured as an integrated bipolar pace/shock lead.

The right ventricular lead system 104 includes an SVC-coil 116, an RV-coil 114, and an RV-tip electrode 112. The RV-coil 114, which may alternatively be configured as an RV-ring electrode, is spaced apart from the RV-tip electrode 112, which is a pacing electrode for the right ventricle.

The right atrial lead system 105 includes an RA-tip electrode 156 and an RA-ring electrode 154. The RA-tip 156 and RA-ring 154 electrodes may provide respectively pacing pulses to the right atrium of the heart and detect cardiac signals from the right atrium. In one configuration, the right atrial lead system 105 is configured as a J-lead.

In this configuration, the intracardiac lead system 102 is shown positioned within the heart 101, with the right ventricular lead system 104 extending through the right atrium 120 and into the right ventricle 118. In particular, the RV-tip electrode 112 and RV-coil electrode 114 are positioned at appropriate locations within the right ventricle 118. The SVC-coil 116 is positioned at an appropriate location within the right atrium chamber 120 of the heart 101 or a major vein leading to the right atrium chamber 120 of the heart 101. The RV-coil 114 and SVC-coil 116 depicted in FIG. 1 are defibrillation electrodes.

The left atrial/left ventricular lead system 106 includes a coronary vein (CV) electrode 126 positioned within a coronary vein of the heart 101 and adjacent multiple heart chambers. The CV electrode 126 may be located, for example, in the coronary sinus 150 of the heart and adjacent to one or more heart chambers for detecting cardiac signals originating in one or more heart chambers. Additionally, or alternatively, one or more coronary vein electrodes may be positioned in a middle cardiac vein, a left posterior vein, a left marginal vein, a great cardiac vein or an anterior vein.

An LV-tip electrode 113, and an LV-ring electrode 117 are inserted through the coronary venous system and positioned adjacent to the left ventricle 124 of the heart 101. The LV-ring electrode 117 is spaced apart from the LV-tip electrode 113, which is a pacing electrode for the left ventricle. The LV-tip 113 and LV-ring 117 electrodes may also be used for sensing the left ventricle. The left atrial/left ventricular lead system 106 further includes an LA-tip 136 and LA-ring 134 electrode positioned adjacent the left atrium 122 for pacing and sensing the left atrium 122 of the heart 101.

The left atrial/left ventricular lead system 106 includes endocardial pacing leads that are advanced through the superior vena cava (SVC), the right atrium 120, the valve of the coronary sinus, and the coronary sinus 150 to locate the LA-tip 136, LA-ring 134, LV-tip 113 and LV-ring 117 electrodes at appropriate locations adjacent to the left atrium and ventricle 122, 124, respectively. In one example, left atrial/ventricular lead placement involves creating an opening in a percutaneous access vessel, such as the left subclavian or left cephalic vein. The left atrial/left ventricular lead 106 is guided into the right atrium 120 of the heart via the superior vena cava.

From the right atrium 120, the left atrial/left ventricular lead system 106 is deployed into the coronary sinus ostium, the opening of the coronary sinus 150. The lead system 106 is guided through the coronary sinus 150 to a coronary vein of the left ventricle 124. This vein is used as an access pathway for leads to reach the surfaces of the left atrium 122 and the left ventricle 124 which are not directly accessible from the right side of the heart. Lead placement for the left atrial/left ventricular lead system 106 may be achieved via the subclavian vein access and a preformed guiding catheter for insertion of the LV and LA electrodes 113, 117, 136, 134 adjacent the left ventricle 124 and left atrium 122, respectively. In one configuration, the left atrial/left ventricular lead system 106 is implemented as a single-pass lead.

The CV electrode 126 may be positioned in the proximity of the AV groove in such a way as to lie in the proximity of multiple heart chambers. The coronary vein electrode 126 may be located in one of a coronary sinus 150, a middle cardiac vein, a left posterior vein, a left marginal vein, a great cardiac vein or an anterior vein of the patient's heart 101. The CV electrode 126 may be configured as a coil electrode. Alternately, one or more small band electrodes may be positioned in the coronary sinus 150 adjacent to one or more heart chambers 120, 118, 122, 124.

Figure 2:
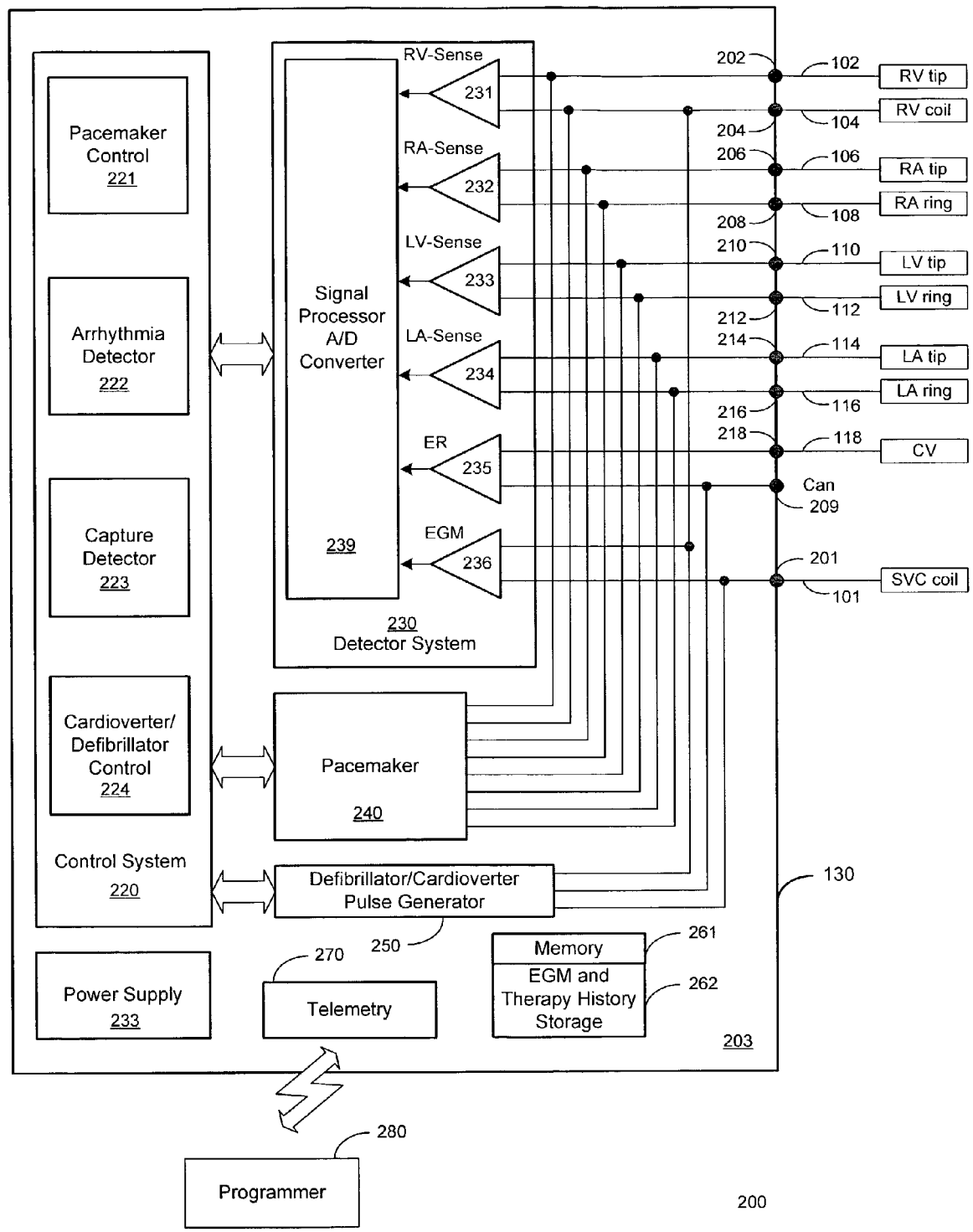
FIG. 2 is a system block diagram of an implantable medical device with which capture verification of the present invention may be implemented.

Referring now to FIG. 2, there is shown an embodiment of a CRM device 200 suitable for implementing a capture verification methodology of the present invention. FIG. 2 shows a CRM device divided into functional blocks. There exist many possible configurations in which these functional blocks can be arranged. The example depicted in FIG. 2 is one possible functional arrangement. The CRM device 200 includes circuitry for receiving cardiac signals from a heart 101 (not shown in FIG. 2) and delivering electrical energy in the form of pace pulses or cardioversion/defibrillation pulses to the heart.

The right ventricular lead system includes conductors 102 and 104 for transmitting sense and pacing signals between terminals 202 and 204 of the CRM device and the RV-tip and RV-coil electrodes, respectively. The right ventricular lead system further includes conductor 101 for transmitting signals between the SVC coil and terminal 201 of the CRM device 200. The right atrial lead system includes conductor 106 for transmitting signals between the RA-tip electrode and terminal 206 and conductor 108 for transmitting signals between the RA-ring electrode and terminal 208.

The left atrial/ventricular lead system includes conductors 110, 112 for transmitting sense and pacing signals between terminals 210, 212 of the CRM device 200 and LV-tip and LV-ring electrodes respectively. The left atrial/ventricular lead system also includes conductor 118 for transmitting sense signals between terminal 218 of the CRM device 200 and the CV electrode. A can electrode 209 coupled to a housing 130 of the CRM device 200 is also provided.

In one embodiment, the CRM device circuitry 203 is encased in a hermetically sealed housing 130 suitable for implanting in a human body. Power to the CRM device 200 is supplied by an electrochemical battery 233 that is housed within the CRM device 200. In one embodiment, the CRM circuitry 203 is a programmable microprocessor-based system, including a control system 220, detector system 230, pacemaker 240, cardioverter/defibrillator pulse generator 250 and a memory circuit 261. The memory circuit 261 stores parameters for various pacing, defibrillation, and sensing modes and stores data indicative of cardiac signals received by other components of the CRM circuitry 203. A memory is also provided for storing historical EGM and therapy data 262, which may be used on-board for various purposes and transmitted to an external programmer unit 280 as required.

The control system 220 may use various control subsystems including pacemaker control 221, cardioverter/defibrillator control 224, capture detector 223, and arrhythmia detector 222. The control system 220 may encompass additional functional components (not shown) for controlling the CRM circuitry 203. The control system 220 and memory circuit 261 cooperate with other components of the CRM circuitry 203 to perform operations involving capture verification according to the principles of the present invention, in addition to other sensing, pacing and defibrillation functions.

Telemetry circuitry 270 is additionally coupled to the CRM circuitry 203 to allow the CRM device 200 to communicate with an external programmer unit 280. In one embodiment, the telemetry circuitry 270 and the programmer unit 280 use a wire loop antenna and a radio frequency telemetric link to receive and transmit signals and data between the programmer unit 280 and telemetry circuitry 270. In this manner, programming commands may be transferred to the CRM circuitry 203 from the programmer unit 280 during and after implant. In addition, stored cardiac data pertaining to capture verification and capture threshold, along with other data, may be transferred to the programmer unit 280 from the CRM device 200, for example.

Cardiac signals derived from the right ventricle may be detected as a voltage developed between the RV-tip electrode and the RV-coil in a bipolar sensing configuration. RV-tip and RV-coil electrodes are shown coupled to an RV-sense amplifier 231 located within the detector system 230. Rate channel signals received by the RV-sense amplifier 231 are communicated to the signal processor and A/D converter 239. The RV-sense amplifier 231 serves to sense and amplify the rate channel signals. The signal processor and A/D converter 239 convert the R-wave signals from analog to digital form and communicate the signals to the control system 220.

Signals derived from the right ventricle may also be detected as a voltage developed between the RV-tip electrode and the can electrode 209. Cardiac signals may also be detected as a voltage developed between the RV-coil and the SVC-coil coupled to the can electrode 209. Signals developed using appropriate combinations of the RV-coil, SVC-coil, and can electrode 209 are sensed and amplified by a shock EGM amplifier 236 located in the detector system 230. The output of the EGM amplifier 236 is coupled to the control system 220 via the signal processor and A/D converter 239.

Signals derived from the left ventricle may be detected as a voltage developed between the LV-tip electrode and the LV-ring electrode in a bipolar sensing configuration. LV-tip and LV-ring electrodes are shown coupled to an LV-sense amplifier 233 located within the detector system 230. Signals received by the LV-sense amplifier 233 are communicated to the signal processor and A/D converter 239. The LV-sense amplifier 233 serves to sense and amplify the signals. The signal processor and A/D converter 239 convert the R-wave signals from analog to digital form and communicate the signals to the control system 220.

Although the embodiment described in the paragraph above involves a bipolar sensing configuration, unipolar sensing is also possible. In unipolar sensing, signals derived from the left ventricle may be detected as a voltage developed between the LV-tip electrode or the LV-ring electrode and the can electrode 209, for example. These unipolar signals may be appropriately sensed and amplified similarly to the method described for the bipolar sensing configuration illustrated in FIG. 2.

RA-tip and RA-ring electrodes are shown coupled to an RA-sense amplifier 232 located within the detector system 230. Atrial sense signals received by the RA-sense amplifier 232 in the detector system 230 are communicated to an A/D converter 239. The RA-sense amplifier serves to sense and amplify the A-wave signals of the right atrium. The A/D converter 239 converts the sensed signals from analog to digital form and communicates the signals to the control system 220.

A-wave signals originating in the left atrium are sensed by the LA-tip and LA-ring electrodes. The A-waves are sensed and amplified by the LA-sense amplifier 234 located in the detector system. The LA-sense amplifier serves to sense and amplify the A-wave signals of the left atrium. The A/D converter 239 converts the sensed signals from analog to digital form and communicates the signals to the control system 220.

Alternatively, unipolar atrial sense signals may be derived from voltages developed between the RA-tip, RA-ring, LA-tip or LA-ring electrodes and the can electrode 209. These unipolar signals may be appropriately sensed and amplified similarly to the method described for the bipolar sensing configuration illustrated in FIG. 2.

The pacemaker 240 communicates pacing signals to the pacing electrodes, RV-tip, RA-tip, LV-tip and LA-tip, according to a pre-established pacing regimen under appropriate conditions. Blanking circuitry (not shown) is employed in a known manner when ventricular or atrial pacing pulses are delivered, such that the ventricular channels, atrial channels, and shock channel are properly blanked at the appropriate time and for the appropriate duration.

Far-field and/or near-field signals developed between the CV-coil and can electrode 209 are used to detect the evoked response (ER) following a pace pulse applied to any heart chamber or any combination of the heart chambers. The CV-coil and can electrode 209 are coupled through an ER amplifier 235 to the signal processor and A/D converter 239 located in the detector system 230. The ER amplifier serves to sense and amplify the evoked response signals. The A/D converter 239 converts the sensed signals from analog to digital form and communicates the signals to the control system 220. The ER signals are coupled to capture detector circuitry 223 within the control system 220.

The output of the capture detector circuitry 223 communicates with the pacemaker control 221 for control of backup pacing. If an evoked response is not detected following a pace pulse, the pacemaker control 221 may initiate a backup pace pulse.

As previously discussed, one or more electrodes inserted in the coronary sinus or in other locations accessible through the coronary venous system may be positioned adjacent to one or more chambers of the heart. An evoked response signal sensed by the coronary vein electrode may be used to detect capture in any of the four heart chambers individually, or in multiple heart chambers following simultaneous or phased pace pulses. An evoked response signal may be generated by delivering a pace pulse to a single chamber or multiple chambers at a level higher than the capture threshold.

Figure 3:
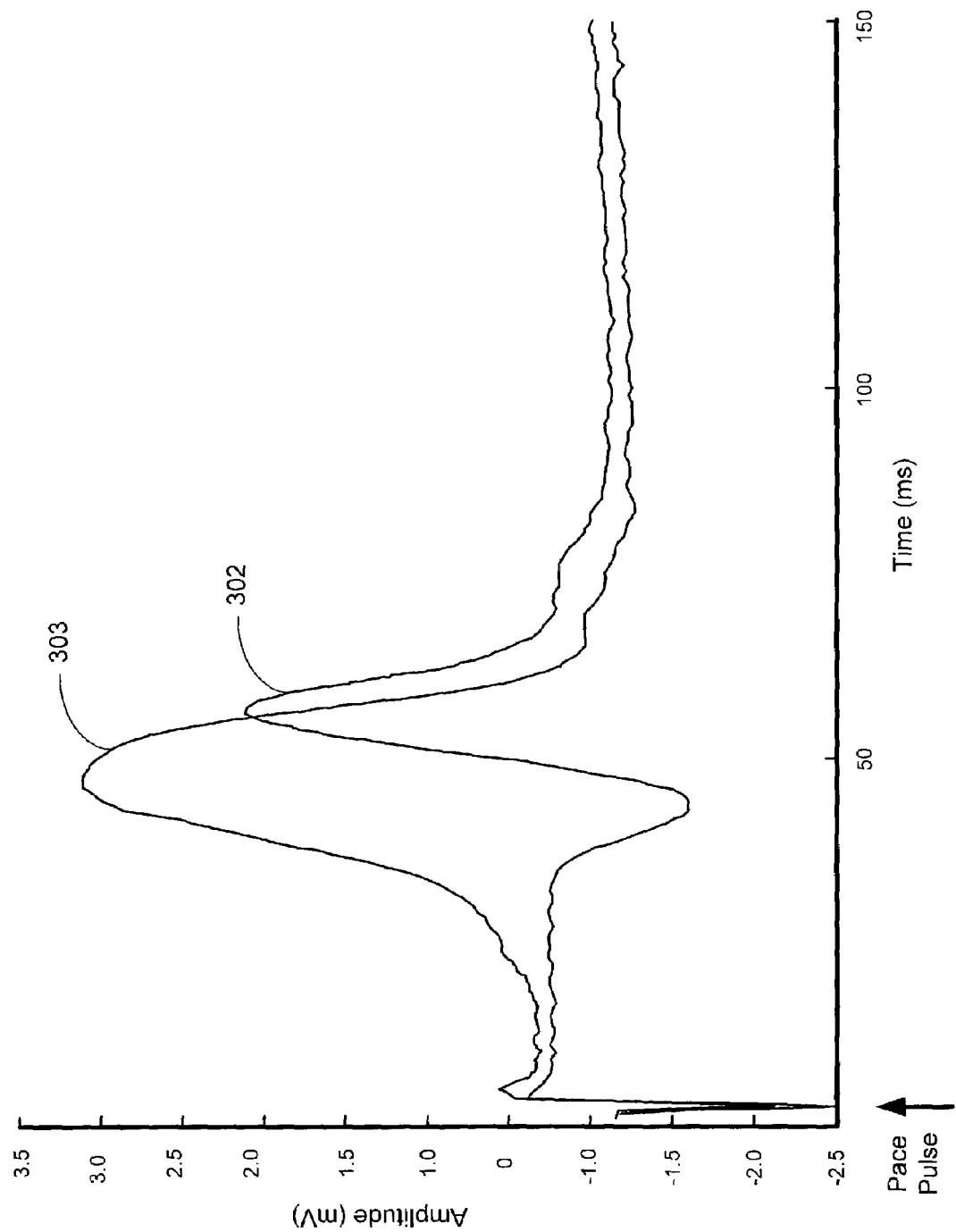
FIG. 3 is a number of graphs illustrating evoked response waveforms sensed using a coronary sinus electrode in accordance with an embodiment of the invention.

The morphology of an evoked response from any individual chamber or from multiple chambers sensed at a coronary vein (CV) electrode is repeatable during a specific time window following a pace pulse. FIG. 3 illustrates a representative evoked response signal 302 resulting from a left ventricle only pace pulse, and a representative evoked response signal 303 resulting from a bi-ventricular pace pulse. Cardiac signals, such as the evoked responses 302, 303 represented in the graphs of FIG. 3, are sensed at the coronary vein electrode, amplified in the ER amplifier, processed and digitized by the CRM detector circuitry, and presented to the capture detector in the control system of the CRM device.

Capture detection may be implemented in the capture detector 223, shown in FIG. 2, using various techniques. In one embodiment, the capture detector determines capture has occurred by comparing an amplitude of the sensed cardiac signal within a specified time window following the stimulation pulse to an amplitude associated with an evoked response. If the sensed cardiac signal achieves the amplitude associated with the evoked response, indicating capture of multiple chambers, the capture detector determines that capture has occurred. Furthermore, the capture detector may detect various features of a cardiac waveform consistent with a given evoked response morphology to determine if capture occurs at each pacing site. An exemplary set of features that may be used to determine capture include a slope of the cardiac signal, timing of local maxima or minima of the cardiac signal, the rise time and/or fall times of the cardiac signal, or a curvature of the cardiac signal. Other features of the cardiac signal may also be used to determine capture. Furthermore, one or more time intervals between cardiac signal features may also be used to determine capture.

Capture may also be determined by comparing a cardiac signal produced by a stimulus pulse and an evoked response template. The evoked response template is a representative evoked response waveform, sensed using the coronary vein electrode, for the multiple chambers paced. Multiple evoked response templates may be created for each possible scenario. For example, evoked response templates may be created for right ventricular capture, left ventricular capture, and biventricular capture in conventional biventricular pacing. By this method, a cardiac signal sensed at the CV electrode is sampled at a predetermined sample rate. All or a portion of the samples of the cardiac signal may be compared to corresponding samples of the evoked response template. If the sensed cardiac signal is comparable to the evoked response template for an individual chamber or multiple chambers, capture of the individual or multiple chambers may be confirmed.

Multiple heart chambers may be paced synchronously or in phased time sequence to provide an appropriate therapy to the heart. When multiple chambers are paced, capture may occur in a single heart chamber, multiple heart chambers, or not at all. By the methods of the present invention, capture in a single chamber may be detected and discriminated from multiple chamber capture. For example, bi-ventricular pacing includes pacing both the right and the left ventricles. By the methods of the present invention, the coronary vein electrode may be used to detect capture in the right ventricle only, the left ventricle only, or both the left and the right ventricles in response to pacing pulses applied to the left and right ventricles in simultaneous or phased time sequence. The methods of the present invention may also be used to differentiate between capture in multiple heart chambers and capture in a single heart chamber.

Figure 4:
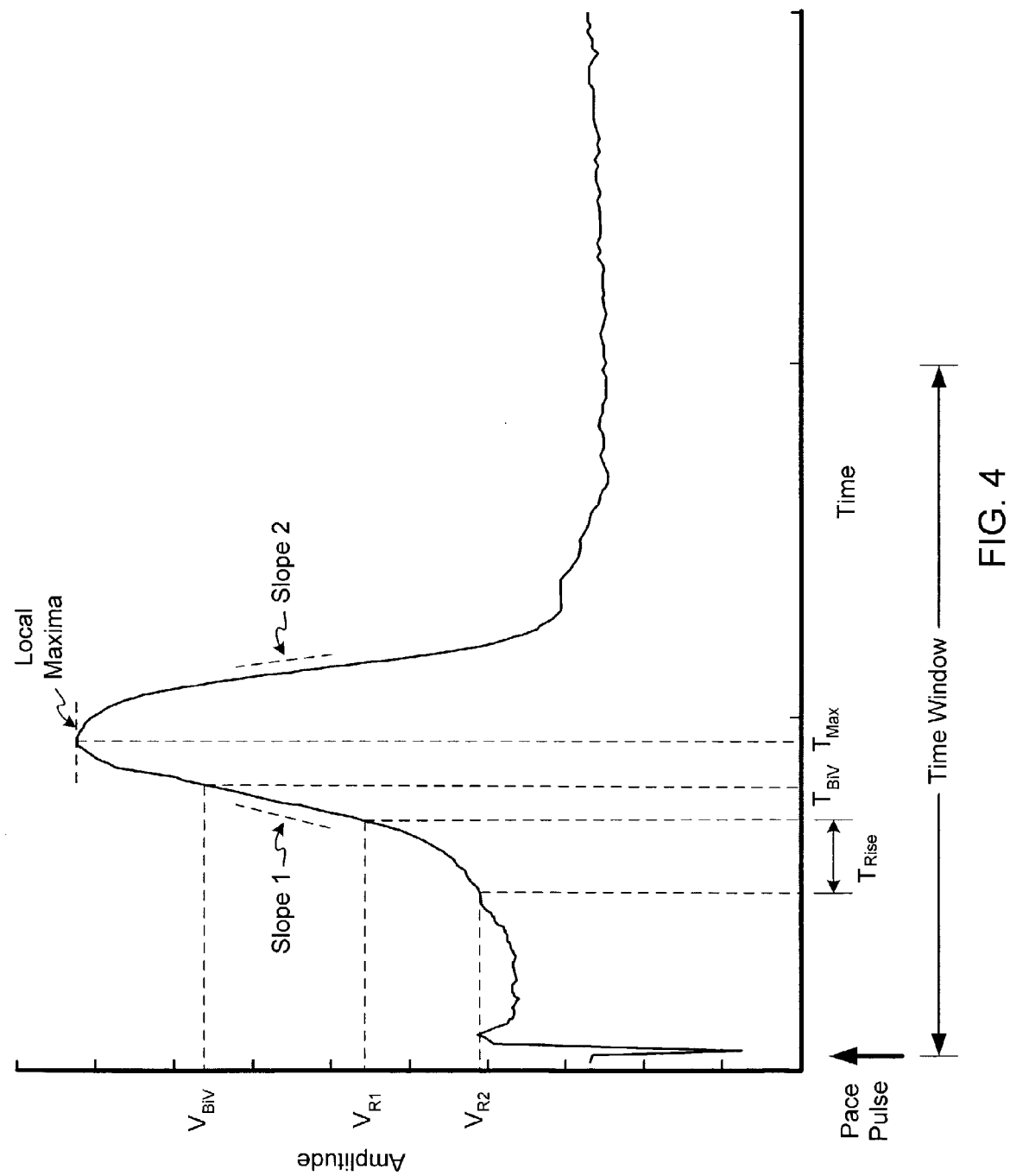
FIG. 4 is a graph illustrating various implementations of capture detection in accordance with an embodiment of the invention.

The implementations of capture detection discussed above are illustrated in FIG. 4. FIG. 4 is a graph of a cardiac signal produced by bi-ventricular stimulation. Capture may be verified, for example, by detecting a predetermined signal amplitude, $V_{BiV}$, that is indicative of an evoked response within a specified time window following the pace pulses. The time window may begin at the application of the stimulation signal and extend for a predetermined time interval. Alternatively, or additionally, capture may be verified by comparing the time $T_{max}$ of a local extrema of the waveform to the timing of a bi-ventricular evoked response local extrema.

Capture may also be detected by when a positive slope of the waveform, Slope 1, or a negative slope of the waveform, Slope 2, achieves a value associated with an evoked response. Furthermore, capture may be detected when a rise time, $T_{Rise}$, of the cardiac signal between predetermined signal amplitudes, for example, $V_{R1}$ and $V_{R2}$, is consistent with the rise time of an evoked response. Capture may also be detected when a curvature of the cardiac signal is consistent with a curvature characteristic of an evoked response.

The presence of one or more of the above cardiac signal features that are consistent with the evoked response may be used to determine capture. In addition, time intervals between two or more cardiac signal features may be used to determine capture.

The morphology of the cardiac signal shown in FIG. 4 may vary depending upon the number and identity of the heart chambers captured by the pace pulses. For example, the morphology of a cardiac signal resulting from capture of a single chamber will generally present a morphology different from the morphology of a cardiac signal resulting from capture of multiple chambers. These differences in cardiac signal morphology may be used to differentiate capture in multiple chambers from capture in a single chamber.

Figure 5:
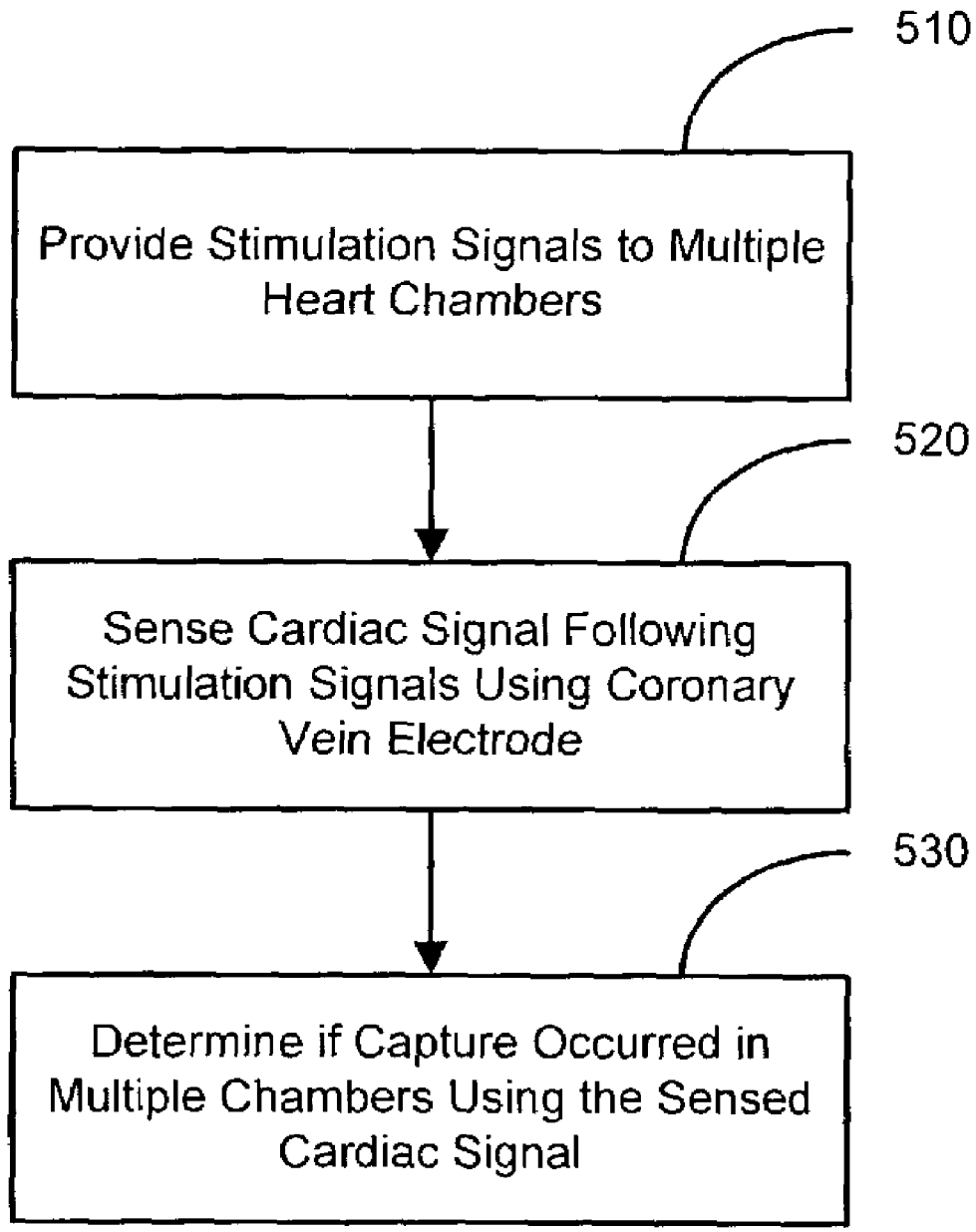
FIG. 5 is a flowchart illustrating a method of detecting capture in multiple heart chambers in accordance with an embodiment of the present invention.

A method for determining capture in multiple heart chambers according to an embodiment of the invention is illustrated in the flowchart of FIG. 5. Stimulation signals are provided 510 to two or more heart chambers. The stimulation signals may be applied, for example, simultaneously or in accordance with an appropriate phased time sequence. The cardiac response following the stimulation signals is detected 520 using an electrode inserted in the coronary venous system of the heart. Capture in the two or more chambers is determined 530 using the cardiac signal sensed by the coronary vein electrode.

As previously discussed, capture may be determined by sensing a cardiac signal at the CV electrode following a pace pulse and comparing the cardiac signal in various ways to known evoked response waveforms at the CV electrode. In one example, capture may be detected when the cardiac signal sensed at the CV electrode reaches a predetermined amplitude indicative of an evoked response signal during a time window following a pace pulse.

Figure 6:
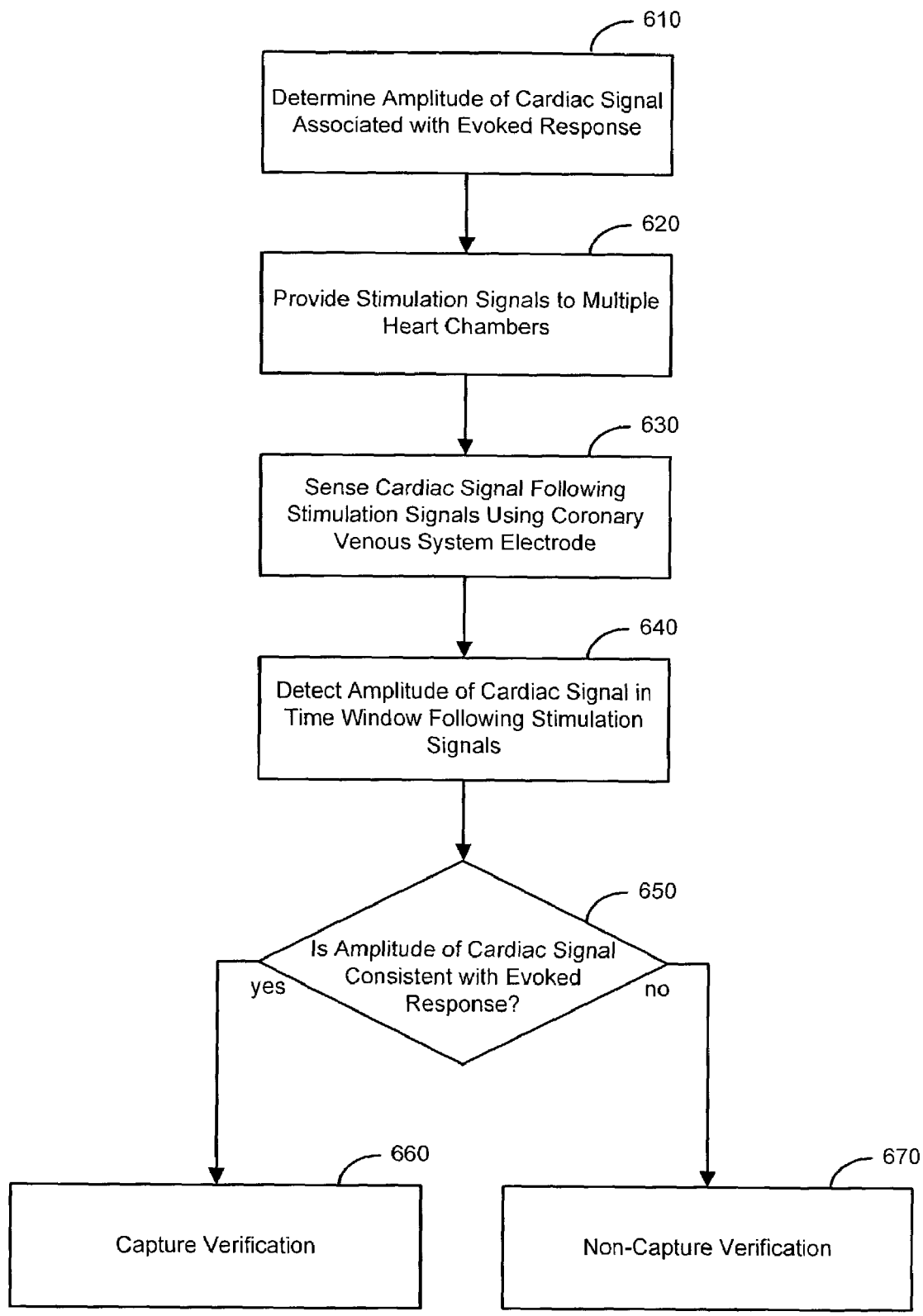
FIG. 6 is a flowchart illustrating a method of detecting capture in multiple heart chambers using a maximum amplitude in a time window of a cardiac signal sensed at a coronary vein electrode in accordance with an embodiment of the invention.

The flowchart of FIG. 6 illustrates a method of capture verification by comparison of an amplitude consistent with an evoked response to the amplitude of a cardiac signal sensed at the CV electrode following a pace pulse. According to this method, the characteristic amplitude of an evoked response of the multiple chambers sensed at the CV electrode is determined 610. A stimulus pulse is applied to the multiple heart chambers 620. The cardiac signal responsive to the stimulus pulse is sensed using the CV electrode 630. The amplitude of the sensed cardiac signal is measured within a predetermined time window following the stimulus pulse 640. If the amplitude of the cardiac signal is consistent with the characteristic amplitude of an evoked response by the multiple heart chambers 650, capture is verified 660. If the amplitude of the cardiac signal is not consistent with the characteristic amplitude of an evoked response 650, a condition of non-capture is detected 670.

A cardiac signal may be characterized by a set of features taken from the signal waveform. An exemplary set of features that may be used to characterize a cardiac signal waveform include the slope of the waveform at particular coordinates, the rise time of the signal, or the time of a local extrema of the cardiac signal waveform. Other features including first and second derivatives, for example, may also be useful in characterizing the waveform for capture detection.

Capture in one or multiple heart chambers may be determined by comparing features of a cardiac signal detected at the CV electrode to features representative of an evoked response waveform detected at the CV electrode. The features of an evoked response waveform indicative of capture in a single heart chamber may be differentiated from the features of an evoked response waveform indicative of capture in multiple heart chambers. A number of evoked response waveforms indicative of capture may be acquired and averaged or otherwise combined with previously acquired features to update the features used to represent an evoked response in the single or multiple heart chambers.

Figure 7:
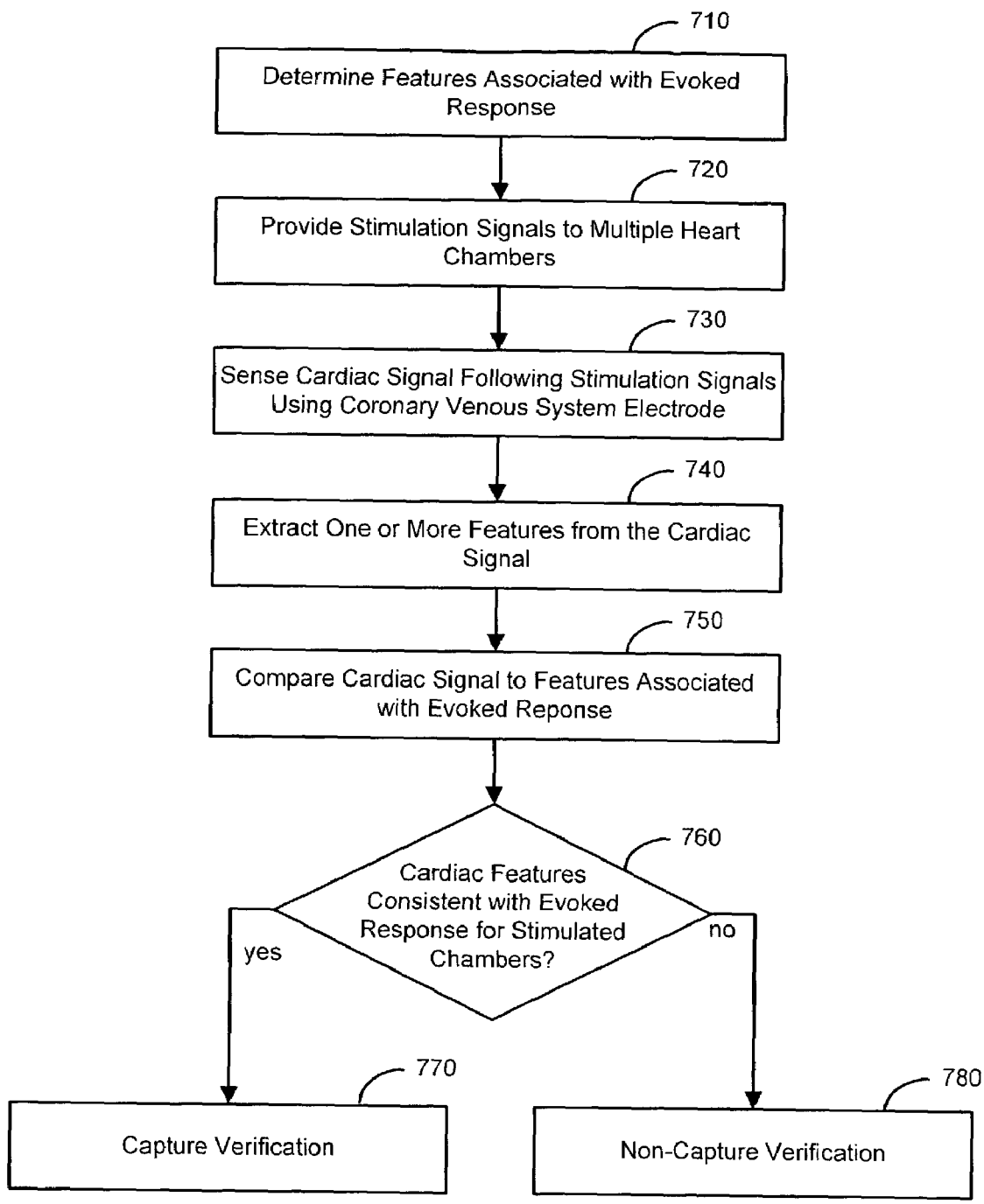
FIG. 7 is a flowchart illustrating a method of detecting capture in multiple heart chambers using one or more features of a cardiac signal sensed at a coronary vein electrode in accordance with an embodiment of the invention.

FIG. 7 illustrates a method of detecting capture by comparing the features of an evoked response with the features of a cardiac signal responsive to a stimulus pulse in accordance with an embodiment of the invention. One or more features of a cardiac signal representative of an evoked response by two or more heart chambers are determined 710. Stimulation pulses are applied to two or more chambers of the heart 720. The cardiac signal responsive to the stimulation pulses is sensed at a CV electrode 730. Features of the cardiac signal are determined 740 and compared to the features of an evoked response 750. If the features of the cardiac signal are consistent with features of an evoked response 760, capture in the multiple chambers is detected 770. If the features of the cardiac signal are not consistent with features of an evoked response 760, capture is not detected 780.

A template characterizing an evoked response following pace pulses applied to the heart may be determined for each individual heart chamber and for multiple heart chambers. The templates may be used to verify capture in an individual heart chamber or in multiple heart chambers. Thus, each individual heart chamber as well as multiple heart chambers may be associated with an evoked response template. An evoked response template for an individual chamber or multiple chambers may be determined, for example, by delivering a pulse to each paced heart chamber or chambers at a voltage greater than the capture threshold. If multiple chambers are paced, pace pulses may be applied simultaneously or closely phased in time to the paced heart chambers. An evoked response waveform produced by the high energy pulses may be stored for each chamber and for multiple chambers as an initially determined evoked response template for the chamber or chambers. Additional evoked response waveforms for individual or multiple heart chambers may be produced and averaged or otherwise combined with the initially determined evoked response templates to update the templates. Capture in an individual chamber or in multiple chambers may be determined by comparing the evoked response template for the chamber or chambers to a cardiac signal sensed at the CV electrode following a pace pulse to the chamber or chambers.

Figure 8:
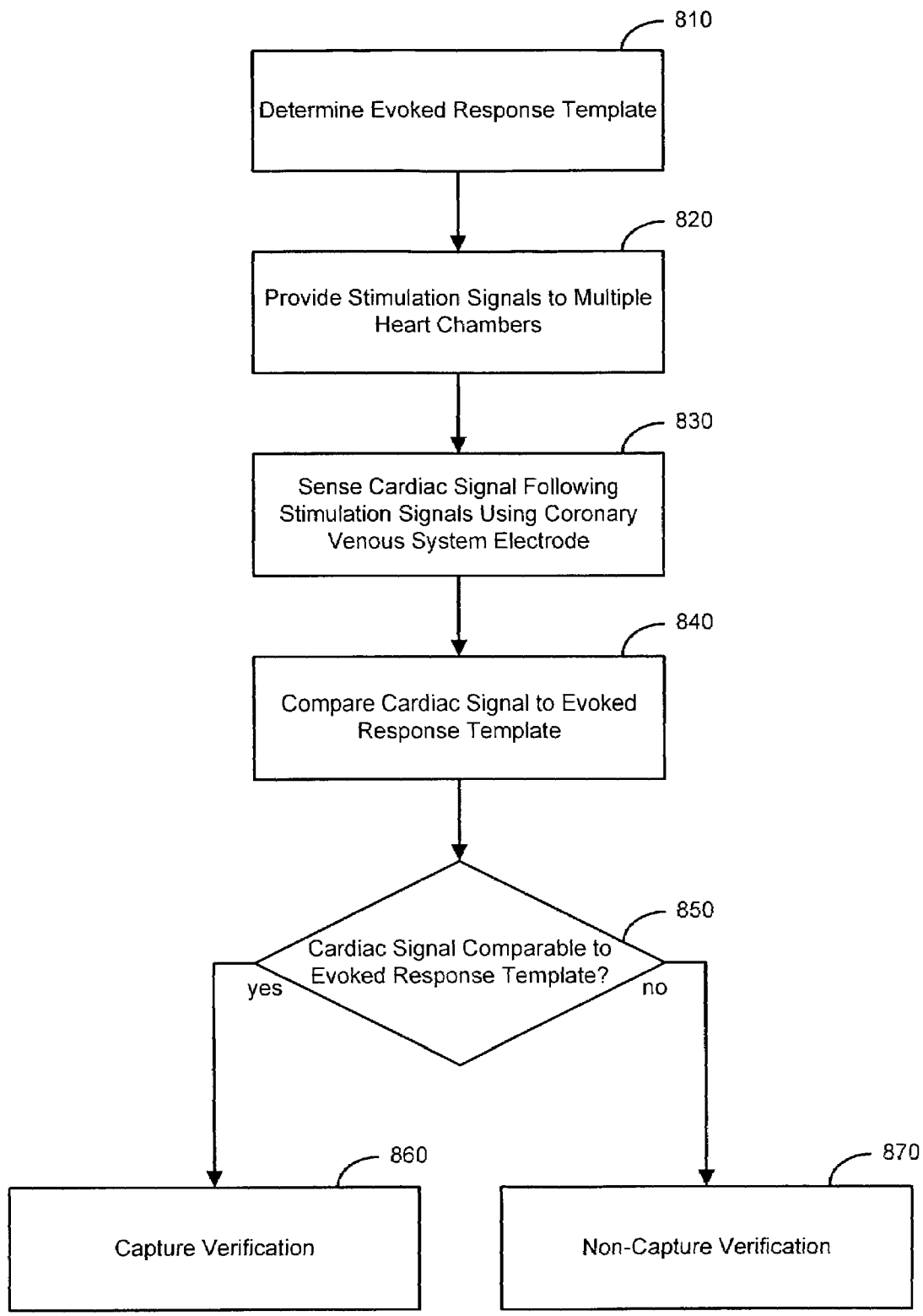
FIG. 8 is a flowchart illustrating a method of detecting capture in multiple heart chambers by comparing an evoked response template to a cardiac signal sensed at a coronary vein electrode in accordance with an embodiment of the invention.

A method for determining capture in multiple heart chambers by comparison of a template to a cardiac waveform is illustrated in the flowchart of FIG. 8. An evoked response template is determined by pacing the multiple heart chambers at an energy level higher than the capture threshold. The cardiac signal resulting from the application of the high energy pace pulses is detected using the CV electrode and stored as an evoked response template 810. The multiple chambers of the heart are paced 820 and the responsive cardiac signal is sensed using the CV electrode 830. Samples of the cardiac signal are compared to samples of the previously stored template 840. If the cardiac signal is comparable to the evoked response template 850, then capture in the multiple chambers is verified 860. If the cardiac signal is not comparable to the evoked response waveform 850, the stimulation pulse did not capture the multiple heart chambers and non-capture is verified 870.

Figure 9:
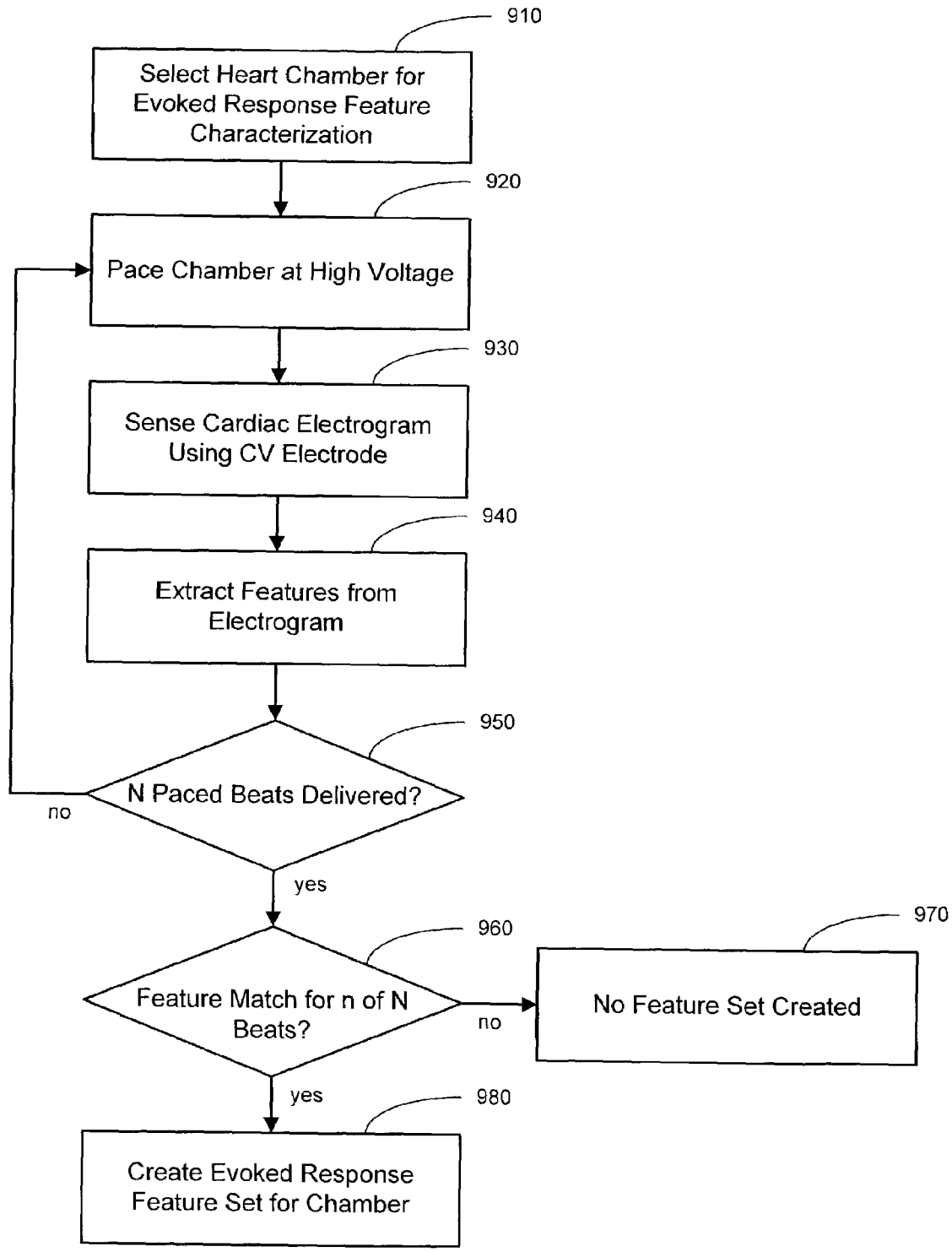
FIG. 9 is a flowchart illustrating a method of creating a feature set representative of an evoked response for individual heart chambers in accordance with an embodiment of the invention.

The flowchart of FIG. 9 illustrates an example method for characterizing one or more cardiac signal features representative of an evoked response for a single heart chamber in accordance with an embodiment of the invention. The feature set characterized by this method may be used to detect capture in the single heart chamber for subsequently applied pace pulses as previously discussed.

A heart chamber is selected for the feature characterization 910 and the selected chamber is paced 920 at high voltage. The pace voltage must be high enough to capture the heart chamber and produce an evoked response. The evoked responses produced by the pace pulses may be analyzed and used to characterize a cardiac signal feature set representative of an evoked response.

The electrogram of the cardiac signal responsive to the high voltage pace pulse is sensed 930 using a coronary vein electrode arranged to sense cardiac signals in the selected chamber. One or more features are extracted 940 from the electrogram and stored. For example, the features extracted and stored may include a slope of the cardiac signal, a timing of local maxima or minima of the cardiac signal, the rise time and/or fall times of the cardiac signal, or a curvature of the cardiac signal. The processes of blocks 920–940 may be repeated until a predetermined number of pace pulses have been delivered 950 and the corresponding cardiac signals sensed. The stored features for each sensed cardiac signal may be analyzed to determine if a subset of the beats, for example, about 8 out of 10 beats, are comparable. If the features of the subset of the total number of beats are comparable 960, then an evoked response feature set for capture detection is created 980 from the comparable features for the chamber. The feature set may be used for capture determination for the chamber. If the features of the subset of the total number of beats are not comparable 960, then a feature set for the single chamber is not created 970.

Figure 10:
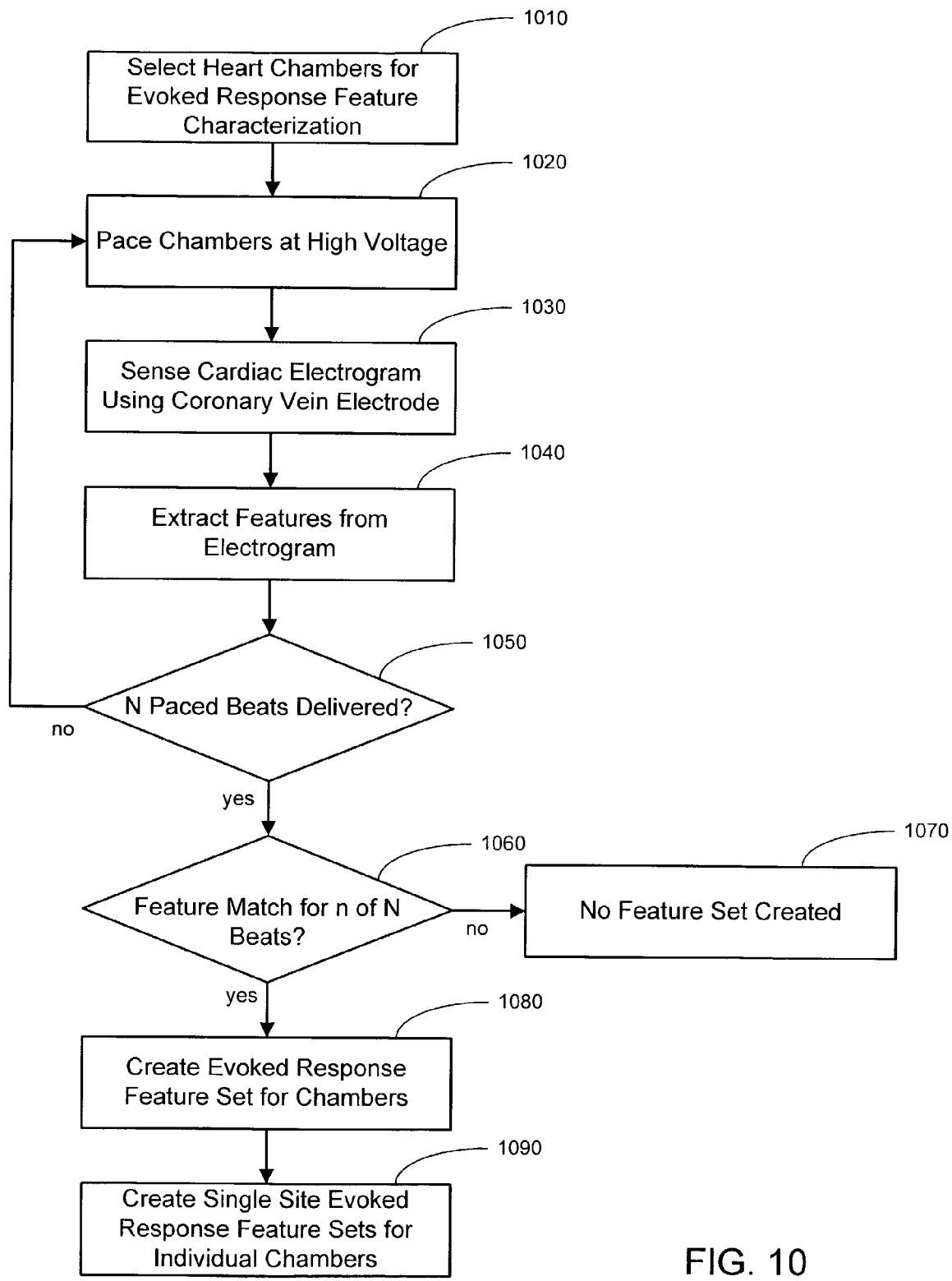
FIG. 10 is a flowchart illustrating a method of creating a feature set representative of an evoked response for multiple heart chambers in accordance with an embodiment of the invention.

The flowchart of FIG. 10 illustrates an example method for characterizing a feature set of one or more cardiac signal features representative of an evoked response for multiple heart chambers in accordance with an embodiment of the invention. The feature set characterized by this method may be used to detect capture in multiple chambers for pace pulses applied to the multiple chambers. The pace pulses may be applied to the heart chambers simultaneously or delivered sequentially within a time period.

Two or more heart chambers are selected for feature characterization 1010. The selected chambers are paced 1020 simultaneously or in closely phased sequence at high voltage. Pacing at full voltage ensures capture of the multiple chambers and allows the characterization of a cardiac signal feature set representative of an evoked response for the multiple chambers. An electrogram of the cardiac signal responsive to the high voltage pace pulses applied to the multiple chambers is sensed 1030 using a coronary vein electrode. The coronary vein electrode is arranged adjacent to the multiple chambers and is capable of sensing cardiac signals from the multiple chambers. One or more features may be extracted 1040 from the electrogram and stored. The process of blocks 1020–1040 may be repeated until a predetermined number of pace pulses, for example N pulses, have been delivered 1050 and the corresponding cardiac signals sensed. The stored features for each sensed cardiac signal may be analyzed to determine if a subset of the beats, for example, about 8 out of 10 beats are comparable. If the features of the subset of the total number of beats are not comparable 1060, then a feature set for the multiple chambers is not created 1070. If the features of the subset of the total number of beats are comparable 1060, then a feature set for capture detection in the multiple chambers is created 1080. In addition, feature sets may be created 1090 for each chamber individually in accordance with the process discussed above and illustrated in FIG. 9.

Periodic capture threshold adjustment may be necessary to maintain effective pacing because the patient's capture threshold may vary over time. A patient's capture threshold in an individual heart chamber or in multiple heart chambers may be periodically assessed through an autocapture procedure initiated by the CRM device.

In accordance with an embodiment of the invention, an autocapture procedure may be performed for multiple heart chambers using cardiac signals detected at a coronary vein electrode. The autocapture procedure for multiple heart chambers may be implemented by ramping down the stimulation energy applied to the heart chambers until a loss of capture is detected in the multiple chambers.

At each stimulation energy, the cardiac signal following the pace pulse is detected and analyzed to determine if the sensed cardiac signal represents an evoked response. A particular stimulation energy may be determined to reliably produce capture if a predetermined percentage of pace pulses at the particular stimulation energy produces an evoked response. The optimum pacing stimulation may then be selected as the lowest pacing energy reliably generating capture plus a reasonable margin of safety.

Figure 11:
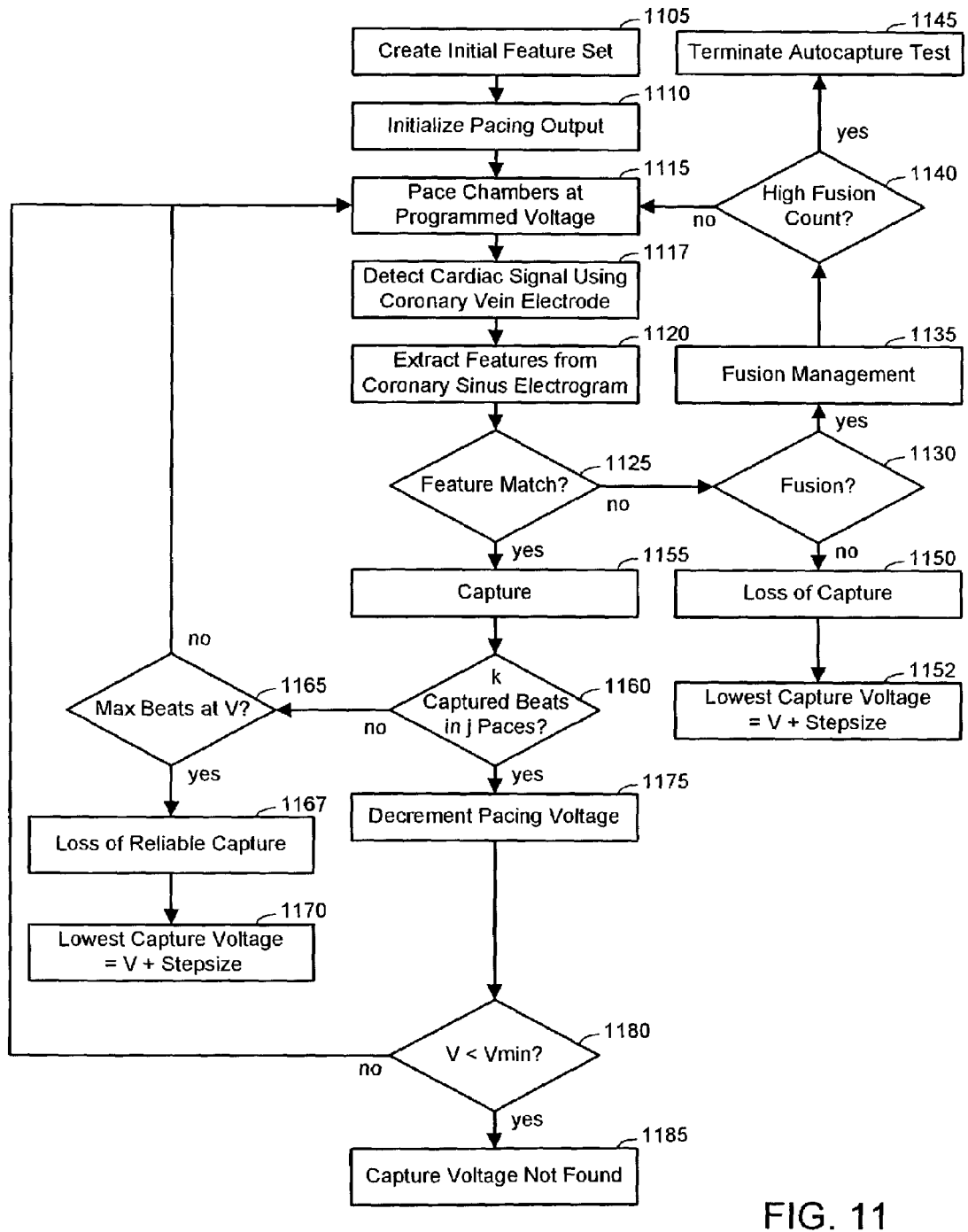
FIG. 11 is a flowchart illustrating a method of performing an autocapture threshold test in accordance with an embodiment of the invention.

FIG. 11 is a flowchart of a method for performing an autocapture procedure for determining the capture threshold of multiple heart chambers in accordance with principles of the invention. An initial feature set is created 1105 for the multiple heart chambers involved in the autocapture test. Characteristic feature sets for detecting capture in multiple or individual heart chambers may be created as discussed above in connection with FIGS. 9 and 10.

The autocapture test may be performed by ramping down the pacing energy from an energy level that ensures capture to a level at which loss of capture is detected. The pacing output is initialized 1110 by programming the pacing output to the maximum pacing energy. Pacing stimulus pulses are delivered 1115 to the heart chambers at the programmed voltage. A cardiac signal responsive to the pacing pulse is sensed 1117 using the coronary sinus electrode. Features of the sensed cardiac signal are extracted 1120 and compared 1125 to one or more features of the characteristic evoked response feature sets for the multiple heart chambers.

If the features of the sensed cardiac signal are comparable 1125 to one or more of the characteristic evoked response features, then capture is detected 1155. Pace pulses at each programmed pacing voltage are applied to the heart for a maximum number of beats to determine if the programmed pacing voltage repeatedly produces capture. If a predetermined number of beats at the programmed voltage produces capture 1160, for example, about 3 captured beats out of 5 beats, then the programmed voltage is determined to reliably produce capture and the pacing voltage is decremented 1175. However, if the maximum number of beats at the programmed voltage are delivered 1165 without producing the predetermined number of captured beats, the programmed voltage does not reliably produce capture 1167. The minimum capture voltage is determined 1170 as the programmed voltage plus the step size.

The process of pacing the selected chambers at successively smaller voltages continues until a lowest capture voltage is determined, or until the programmed voltage falls below a minimum voltage 1180. If the minimum voltage is reached 1180 without detecting a pacing voltage that reliably produces capture, no threshold is found 1185.

If a feature match is not detected 1125 between a cardiac signal produced by a pace pulse and the characteristic features produced by an evoked response, a fusion detection process 1130 is initiated. The cardiac signal is analyzed to determine 1130 if the cardiac beat represents a fusion beat. If the cardiac beat is a fusion beat, then fusion management 1135 may be performed to modify the pacing parameters so that the incidence of fusion is reduced. If the fusion management is not successful, and fusion beats continue to be detected 1140, the autocapture test is terminated 1145. If a feature match is not detected 1125, and fusion is not detected 1130, loss of capture is determined 1150. The lowest capture voltage is established as the programmed voltage plus the step size 1152.

Figure 12:
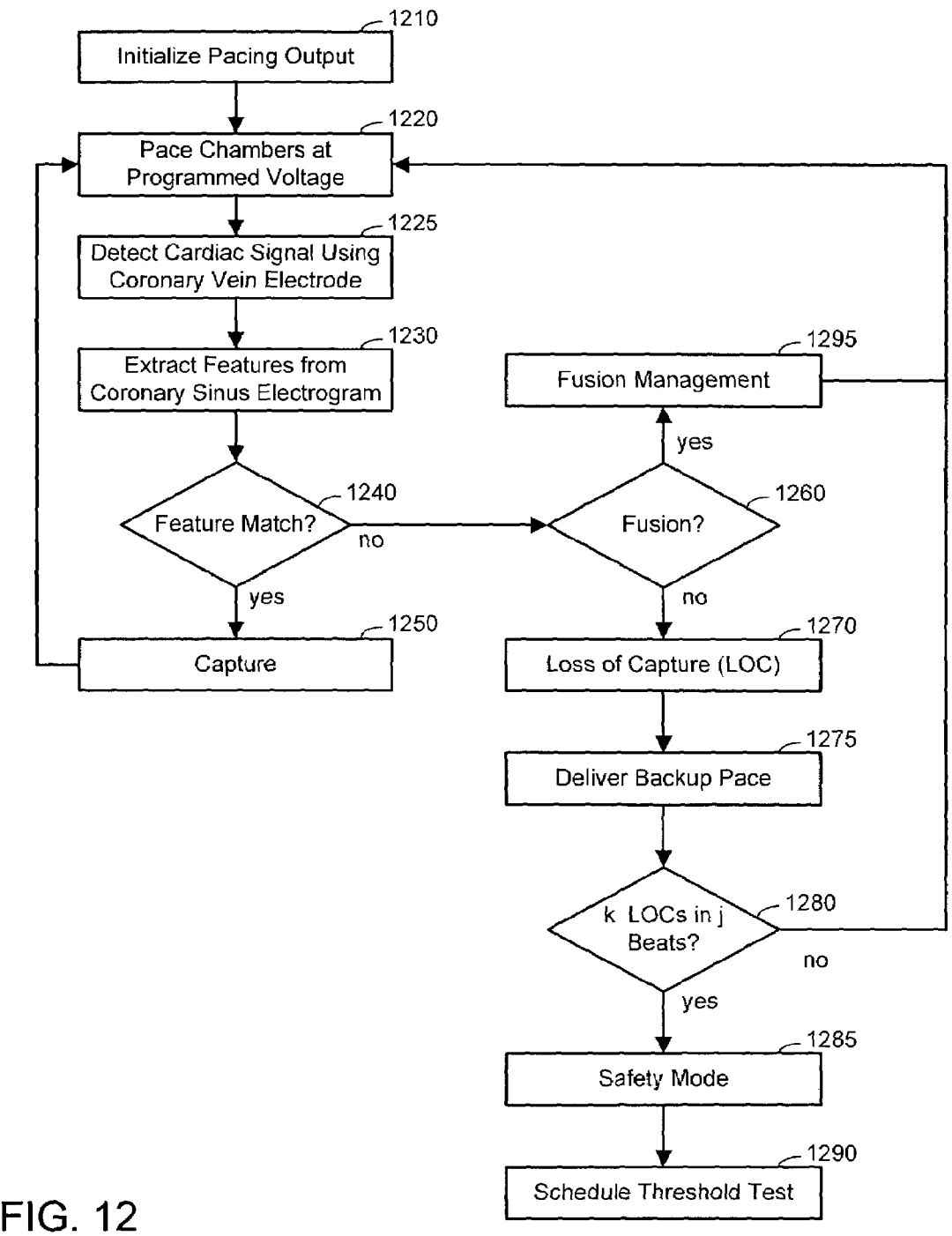
FIG. 12 is a flowchart illustrating a method of performing beat-by-beat monitoring of pacing in accordance with an embodiment of the invention.

A process for beat-by-beat monitoring of pacing to ensure capture is illustrated in the flowchart of FIG. 12. The preceding discussion illustrates a method for performing an autocapture test for multiple heart chambers using cardiac signals sensed at a coronary sinus electrode. The pacing voltage for the multiple chambers may be initialized 1210 to the lowest capture voltage determined by the test plus some margin of safety. The multiple chambers are paced 1220 at the programmed voltage. The cardiac signal following each pace pulse is sensed 1225 at the coronary sinus electrode. One or more features of the sensed cardiac signal are extracted 1230 and are compared to one or more features characteristic of an evoked response. If the one or more features are comparable 1240, capture of the multiple chambers is verified 1250 and pacing at the programmed voltage continues.

If the features of the sensed cardiac signal are not comparable 1240 to the features characteristic of an evoked response, the cardiac signal is analyzed to determine if the beat is a fusion beat. If the beat is a fusion beat 1260, then fusion management processes are initiated 1295 to eliminate or reduce the incidence of fusion.

However, if the cardiac beat is not a fusion beat 1260, then a loss of capture determination is made 1270. The previous pace pulse did not effectively produce a contractile response in the heart chambers. In this situation, back up pulses at a higher voltage are delivered 1275 to the heart chambers.

If loss of capture is repeatedly detected 1280, for example, if about 2 loss of capture episodes are detected in 3 beats, then the programmed pacing voltage may not reliably capture the heart chambers. The CRM begins operating in safety mode 1285, wherein the heart is paced at a high voltage to reliably produce a captured response. A threshold test may be scheduled 1290 to reassess the capture threshold for the multiple chambers.

Figure 13:
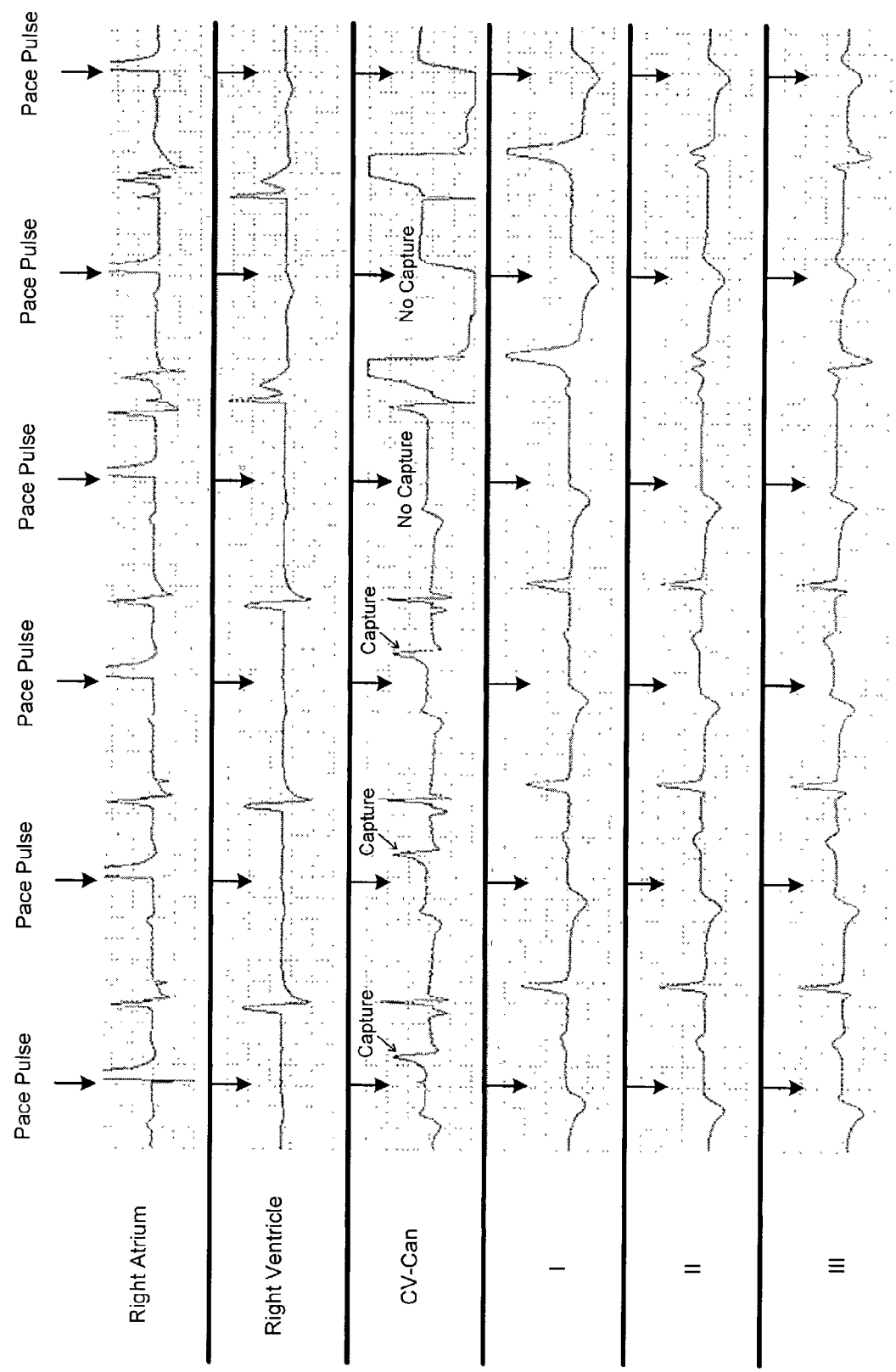
FIG. 13 is a graph of cardiac signals sensed at a coronary vein electrode during an atrial capture threshold test in accordance with an embodiment of the invention.
Figure 14:
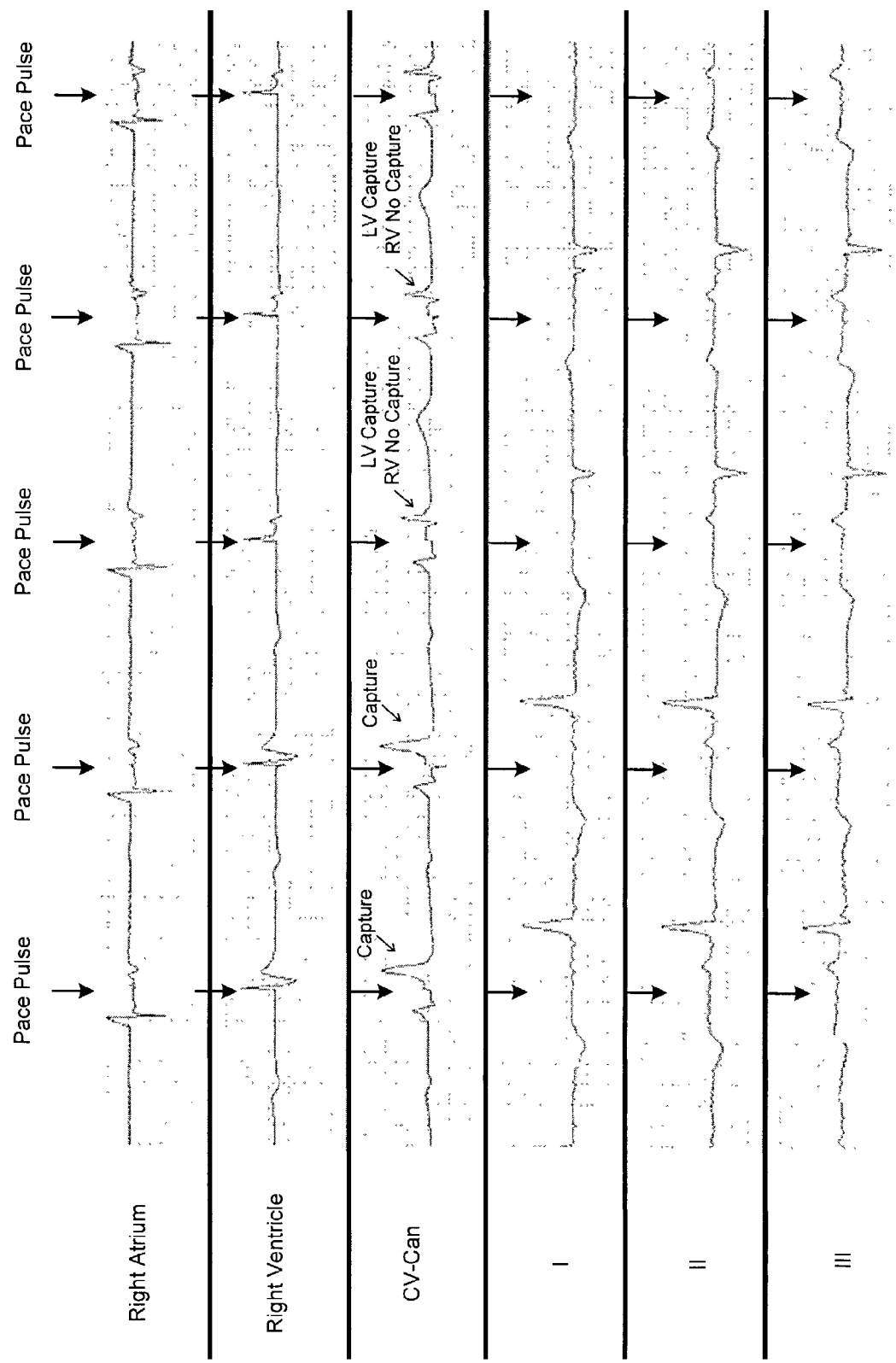
FIG. 14 is a graph of cardiac signals sensed at a coronary vein electrode during a biventricular capture threshold test in accordance with an embodiment of the invention.

FIGS. 13 and 14 are graphs of cardiac signals taken during an atrial capture threshold test and a biventricular capture threshold test, respectively. The graphs labeled CV-Can represent cardiac signals sensed between a CV electrode located in the coronary sinus of the heart and the CRM device can electrode. The CV electrode is positioned so that the CV electrode is adjacent to all four heart chambers. FIG. 13 is a graph of experimental data showing the cardiac signal sensed between CV and can electrodes during an atrial capture threshold test. The atrial capture threshold test steps down the pacing energy applied to the right atrium until loss of capture is detected. As illustrated by the data of FIG. 13, loss of capture is visible in the signals detected using the CV electrode positioned in the coronary sinus. FIG. 14 shows the experimental data acquired during a bi-ventricular capture threshold test. In this example, the CV-Can cardiac signal shows a loss of capture in the right ventricle only.

Various modifications and additions can be made to the preferred embodiments discussed above without departing from the scope of the present invention. Accordingly, the scope of the present invention should not be limited by the particular embodiments described above, but should be defined only by the claims set forth below and equivalents thereof.

What is claimed is:

1. A method of detecting capture in multiple chambers of a patient's heart, comprising:

sensing, through a single sense amplifier channel, a cardiac signal using a coil electrode positioned at a coronary vein location of the patient's heart, the cardiac signal responsive to stimulation signals applied to the multiple heart chambers during a cardiac cycle; and determining if capture occurs with respect to the multiple chambers of the patient's heart using the sensed cardiac signal.

2. The method of claim 1, wherein sensing the cardiac signal comprises sensing the cardiac signal responsive to stimulation signals applied to a left ventricle and a right ventricle of the patient's heart.

3. The method of claim 1, wherein sensing the cardiac signal comprises sensing the cardiac signal responsive to stimulation signals applied to a left atrium and a right atrium of the patient's heart.

4. The method of claim 1, wherein sensing the cardiac signal comprises sensing the cardiac signal responsive to stimulation signals applied to a left atrium and a left ventricle of the patient's heart.

5. The method of claim 1, wherein:
sensing the cardiac signal further comprises sensing an evoked response signal associated with the multiple chambers of the patient's heart in response to the stimulation signals applied to the multiple heart chambers; and
determining if capture occurs further comprises determining, using the evoked response signal, if capture occurs with respect to the multiple heart chambers.

6. The method of claim 1, wherein sensing the cardiac signal comprises sensing the cardiac signal responsive to phased stimulation signals applied to the multiple chambers of the patient's heart.

7. The method of claim 1, wherein sensing the cardiac signal comprises sensing the cardiac signal responsive to simultaneous stimulation signals applied to the multiple chambers of the patient's heart.

8. The method of claim 1, wherein determining if capture occurs further comprises using one or more templates to determine if capture occurs.

9. The method of claim 1, wherein determining if capture occurs further comprises using a first template for determining if capture occurs with respect to a right ventricle, and using a second template for determining if capture occurs with respect to a left ventricle of the patient's heart.

10. The method of claim 1, wherein determining if capture occurs further comprises using a bi-ventricular template for determining if capture occurs with respect to a right ventricle and a left ventricle of the patient's heart.

11. The method of claim 1, wherein determining if capture occurs further comprises using a first template for determining if capture occurs with respect to a right atrium, and using a second template for determining if capture occurs with respect to a left atrium of the patient's heart.

12. The method of claim 1, wherein determining if capture occurs further comprises using a bi-atrial template for determining if capture occurs with respect to a right atrium and a left atrium of the patient's heart.

13. The method of claim 1, wherein determining if capture occurs further comprises detecting if one or more features of the sensed cardiac signal are consistent with an evoked response.

14. The method of claim 13, wherein determining if the one or more features of the sensed cardiac signal are associated with the evoked response comprises determining if a slope of the sensed cardiac signal is consistent with the evoked response.

15. The method of claim 13, wherein determining if the one or more features of the sensed cardiac signal are associated with the evoked response comprises detecting if a timing of a local extrema of the sensed cardiac signal is consistent with the evoked response.

16. The method of claim 13, wherein determining if the one or more features of the sensed cardiac signal are associated with the evoked response comprises detecting if a curvature of the sensed cardiac signal is consistent with the evoked response.

17. The method of claim 13, wherein determining if the one or more features of the sensed cardiac signal are associated with the evoked response comprises detecting if the time interval between the one or more features is consistent with the evoked response.

18. The method of claim 13, wherein determining if the one or more features of the sensed cardiac signal are associated with the evoked response comprises detecting if a rise time or a fall time of the sensed cardiac signal is consistent with a rise time or a fall time of the evoked response.

19. The method of claim 1, wherein determining if capture occurs further comprises detecting if a predetermined amplitude of the sensed cardiac signal falls within a time window associated with an evoked response.

20. The method of claim 19, wherein the time window is a time interval relative to the stimulation signals.

21. A system for detecting capture in multiple chambers of a patient's heart, comprising:
means for sensing, through a single sense amplifier channel, a cardiac signal using a coil electrode positioned at a coronary vein location of the patient's heart, the cardiac signal responsive to stimulation signals applied to the multiple heart chambers during a cardiac cycle; and
means programmed to determine if capture occurs in multiple chambers of a patient's heart using the sensed cardiac signal.

22. The system of claim 21, wherein the multiple chambers comprise a left ventricle and a right ventricle of the patient's heart.

23. The system of claim 21, wherein the multiple chambers comprise a left atrium and a right atrium of the patient's heart.

24. The system of claim 21, wherein:
means for sensing the cardiac signal further comprises means for sensing an evoked response signal associated with the multiple heart chambers in response to the stimulation signals applied to the multiple heart chambers of the patient's heart; and
means for determining if capture occurs further comprises means for determining, using the evoked response signal, if capture occurs with respect to the multiple heart chambers.

25. The system of claim 21, wherein means for determining if capture occurs further comprises means for using one or more templates to determine if capture occurs.

26. The system of claim 21, wherein means for determining if capture occurs further comprises means for detecting if one or more features of the sensed cardiac signal is associated with an evoked response.

* * * * *